United States Patent [19]

Martin et al.

[11]  4,189,537
[45]  Feb. 19, 1980

[54] **PROCESS OF PRODUCING ANTIBIOTIC BL580Δ WITH *STREPTOMYCES HYGROSCOPICUS***

[75] Inventors: John H. E. J. Martin, New City; Martin R. Hertz, Pearl River, both of N.Y.

[73] Assignee: American Cyanamid Company, Stamford, Conn.

[21] Appl. No.: 962,574

[22] Filed: Nov. 20, 1978

Related U.S. Application Data

[60] Division of Ser. No. 756,659, Jan. 4, 1977, Pat. No. 4,138,481, which is a continuation-in-part of Ser. No. 701,395, Jun. 30, 1976, abandoned.

[51] Int. Cl.$^2$ .................................................. C12D 9/14
[52] U.S. Cl. .................................... 435/75; 435/898

[58] Field of Search ..................................... 195/80 R

[56] References Cited

U.S. PATENT DOCUMENTS

| | | | |
|---|---|---|---|
| 3,595,955 | 7/1971 | Boer et al. | 424/121 |
| 3,812,249 | 5/1974 | Martin | 424/121 |
| 4,024,251 | 5/1977 | Maiese et al. | 424/181 |
| 4,132,779 | 1/1979 | Hertz et al. | 424/122 |

*Primary Examiner*—Lionel M. Shapiro
*Attorney, Agent, or Firm*—Edward A. Conroy, Jr.

[57] ABSTRACT

This disclosure describes a new antibiotic designated BL580Δ produced in a microbiological fermentation under controlled conditions using a new strain of *Streptomyces hygroscopicus* and mutants thereof. This new antibiotic is an active anticoccidial agent.

1 Claim, No Drawings

PROCESS OF PRODUCING ANTIBIOTIC BL580Δ WITH STREPTOMYCES HYGROSCOPICUS

CROSS REFERENCE TO RELATED APPLICATION

This is a division of application Ser. No. 756,659, filed Jan. 4, 1977, now U.S. Pat. No. 4,138,481, issued Feb. 9, 1979.

This application is a continuation-in-part of our co-pending application Serial No. 701,395, filed June 30, 1976, abandoned.

BRIEF SUMMARY OF THE INVENTION

This invention relates to a new antibiotic designated BL580Δ, to its production by fermentation, to methods for its recovery and concentration from crude solutions and to processes for its purification. The present invention includes within its scope the antibiotic BL580Δ in dilute form, as a crude concentrate and in its pure crystalline form. The effects of this new antibiotic as an anticoccidial agent together with its chemical and physical properties, differentiate it from previously described antibiotics.

Antibiotic BL580Δ may be represented by the following structural formula which is in accordance with accepted convention in that an α-substituent is behind the plane of the paper and is represented by a—bond whereas a β-substituent is in front of the plane of the paper and is represented by a⬛bond.

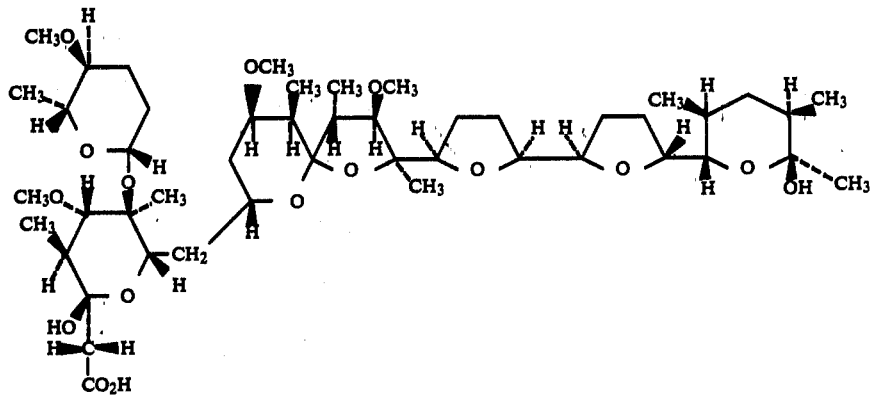

DETAILED DESCRIPTION OF THE INVENTION

The novel antibiotic of the present invention is an organic carboxylic acid and thus is capable of forming salts with non-toxic, pharmaceutically acceptable cations. Thus, salts formed by admixture of the antibiotic free acid with stoichiometric amounts of cations, suitably in a neutral solvent, may be formed with cations such as the sodium ion, potassium ion, calcium ion, magnesium ion, and ammonium ion as well as the organic amine cations such as the tri(lower alkyl)amine cations (e.g. triethylamine, triethanolamine), procaine, and the like. The cationic salts of antibiotic BL580Δ are, in general, crystalline solids, relatively insoluble in water, and soluble in most common organic solvents such as methanol, ethyl acetate, acetone, chloroform, heptane, ether, and benzene.

The new antibiotic which has been designated BL580Δ is formed during the cultivation under controlled conditions of a new strain of *Streptomyces hygroscopicus* which also produces the known antibiotics BL580α and BL580β (see U.S. Pat. No. 3,812,249). This new strain is a mutant derived by treatment of *S. hygroscopicus* NRRL 5647 with N-methyl-N'-nitro-N''-nitrosoguanidine. A viable culture of the new microorganism has been deposited with the Culture Collection Laboratory, Northern Utilization Research and Development Division, United States Department of Agriculture, Peoria, Illinois and has been added to its permanent collection. It is freely available to the public from this depository under its accession number NRRL 8180.

The cultural, physiological and morphological features of NRRL 8180 are substantially the same as those of NRRL 5647 as determined by Dr. H. D. Tresner, Lederle Laboratories Division, American Cyanamid Company, Pearl River, New York. The general description of the microorganism, based on diagnostic characteristics observed, is the same as that for NRRL 5647 published in U.S. Pat. No. 3,812,249, but is reproduced below for convenience.

Observations were made of the cultural, physiological and morphological features of NRRL 8180 in accordance with the methods detailed by Shirling and Gottlieb, Internat. Journ. of Syst. Bacteriol., 16, 313-340 (1966). The underscored descriptive colors and color chip designations are taken from Jacobson, et al., Color Harmony Manual, 3rd Edition (1948), Container Corp. of America, Chicago, Illinois. Descriptive details are recorded in Tables I through IV below.

AMOUNT OF GROWTH

Good on yeast extract, Kuster's oatflake, tomato paste-oatmeal and potato-dextrose agars; moderate on asparagine-dextrose, Hickey and Tresner's, inorganic salts-starch and Bennett's agars; light on Czapek's solution agar.

AERIAL MYCELIUM

Whitish to yellowish, becoming grayish in sporulation zones ranging from Fawn (4 ig) to Beaver (4 li) to Ashes (5 fe). Sporulation zones becoming black and hygroscopic in older cultures.

SOLUBLE PIGMENTS

None on most media; yellowish on yeast extract, Bennett's and potato-dextrose agars and only in light amounts.

REVERSE COLOR

Generally in yellowish shades on most media.

MISCELLANEOUS PHYSIOLOGICAL REACTIONS

Nitrates reduced to nitrites; complete liquefaction of gelatin; no formation of melanoid pigments on peptone-iron agar; complete peptonization of purple milk in 7 days; tolerance of NaCl in growth medium $\leq 7$ percent but $<10$ percent. Carbon source utilization according to the method of Pridham and Gottlieb, J. Bacteriol., 56, 107-114 (1948) as follows: Good utilization of adonitol, d-galactose, d-fructose, d-raffinose, salicin, d-xylose and dextrose; poor or no utilization of d-melezitose, d-melibiose, l-arabinose, i-inositol, lactose, d-mannitol, l-rhamnose, sucrose and d-trehalose.

turns; spores are mostly isodiametric, cylindrical, phalangiform, 0.6–0.7 μm×0.7–0.8 μm. Spores smooth as determined by electron microscopy; spore sheaths finely wrinkled.

On the basis of the general characteristics observed, microorganism NRRL 8180 is a member of a large group of streptomycetes characterized by gray spores, spiral spore chains, smooth-walled spores and lack of melanin pigments. The hygroscopic nature of the culture along with its entire composite of morphological and physiological characteristics makes it a representative strain of *Streptomyces hygroscopicus* as defined by H. D. Tresner and E. J. Backus, "A Broadened Concept of the Characteristics of *Streptomyces hygroscopicus*", *Appl. Microbiol.*, 4, 243-250 (1956) and H. D. Tresner, E. J. Backus and J. A. Hayes, "Morphological Spore Types in the *Streptomyces hygroscopicus*-like Complex", *Appl. Microbiol.*, 15, 637-639 (1967).

Table I

Cultural Characteristics of *Streptomyces hygroscopicus* NRRL 8180
Incubation: 14 days  Temperature: 28° C.

| Medium | Amount of growth | Aerial mycelium and/or spores | Soluble Pigment | Reverse color | Remarks |
|---|---|---|---|---|---|
| Czapeck's solution agar | Light | Trace of whitish aerial mycelium. No sporulation. | None | Colorless to whitish | |
| Yeast extract agar | Good | Aerial mycelium whitish, becoming Fawn (4 ig) to Beaver (4 li) in sporulation zones. Sporulation heavy. | Yellowish, light | Bamboo (2 fb) | Blackish hygroscopic areas in central colony zones. |
| Kuster's oatflake agar | Good | Aerial mycelium whitish, becoming Fawn (4 ig) to Beaver (4 li) in sporulation zones. Sporulation heavy. | None | Light mustard tan (2 ie) | Blackish hygroscopic areas in central colony zones. Yellowish exudate in marginal zones. |
| Asparagin-dextrose agar | Moderate | Aerial mycelium whitish, becoming Ashes (5 fe) to Fawn (4 ig) in sporulation areas. Sporulation moderate. | None | Bamboo (2 fb) | Blackish hygroscopic areas in central colony zones. |
| Hickey and Tresner's agar | Moderate | Aerial mycelium whitish to yellowish, becoming Fawn (4 ig) to Beaver (4 li) in sporulation zones. Sporulation heavy. | None | Bamboo (2 fb) | Extensive hygroscopic areas in central colony zones. |
| Inorganic salts-starch agar | Moderate | Aerial mycelium whitish to yellowish, becoming Fawn (4 ig) to Beaver (4 li) in sporulation zones. Sporulation heavy. | None | Pastel yellow (1 db) | Blackish hygroscopic areas in central colony zones. |
| Tomato-paste oatmeal agar | Good | Aerial mycelium whitish to yellowish, becoming Fawn (4 ig) to Beaver (4 li) in sporulation zones. Sporulation very heavy. | None | Yellow maple (3 ng) | Extensive hygroscopic areas in central colony zones. Yellowish exudate in marginal zones. |
| Bennett's agar | Moderate | Aerial mycelium whitish, becoming Beaver (4 li) in sporulation zones. Sporulation heavy. | Yellowish, light | Bamboo (2 fb) | Blackish hygroscopic areas in central colony zones. |
| Potato-dextrose agar | Good | Aerial mycelium whitish to yellowish becoming Ashes (5 fe) to Fawn (4 ig) in sporulation zones. Sporulation moderate. | Yellowish, light | Yellow maple (3 ng) | Blackish hygroscopic areas in central colony zones. |

MICROMORPHOLOGY

Aerial mycelium gives rise to spore-bearing branches which terminate in tightly coiled spirals of several Table II Micromorphology of *Streptomyces hygroscopicus* NRRL 8180

| Medium | Aerial mycelium and/or sporiferous structures | Spore shape | Spore size | Spore surface |
|---|---|---|---|---|
| Kuster's oatflake agar | Aerial mycelium gives rise to spore bearing | Spores are mostly isodiametric, | 0.6–0.7μm × 0.7–0.8μm | Smooth as determined by electron |

Table II-continued
Micromorphology of *Streptomyces hygroscopicus* NRRL 8180

| Medium | Aerial mycelium and/or sporiferous structures | Spore shape | Spore size | Spore surface |
|---|---|---|---|---|
| | branches which terminate in tightly coiled spirals of several turns. | cylindrical, phalangiform | | microscopy. Spore sheaths finely wrinkled. |

Table III
Miscellaneous Physiological Reactions of *Streptomyces hygroscopicus* NRRL 8180

| Medium | Incubation (28° C.) | Growth amount | Physiological reaction |
|---|---|---|---|
| Organic nitrate broth | 7 Days | Good | Nitrates reduced to nitrites. |
| Organic nitrate broth | 14 Days | Good | Nitrates reduced to nitrites. |
| Gelatin | 7 Days | Good | Complete liquefaction |
| Peptone-iron Agar | 24–48 Hours | Good | No melanoid pigments produced |
| Purple milk | 7 Days | Good | Complete peptonization |
| Yeast extract agar plus (4, 7, 10 and 13%) NaCl | 10 Days | Good | NaCl tolerance ≧7% but <10% |

Table IV
Carbon Source Utilization Pattern of *Streptomyces hygroscopicus* NRRL 8180
Incubation: 10 Days  Temperature: 28° C.

| Carbon Source | Utilization* |
|---|---|
| Adonitol | 3 |
| l-Arabinose | 0 |
| Dextran | 3 |
| d-Fructose | 3 |
| i-Inositol | 0 |
| Lactose | 0 |
| d-Mannitol | 0 |
| d-Melezitose | 1 |
| d-Melibiose | 1 |
| d-Raffinose | 3 |
| l-Rhamnose | 0 |
| Salicin | 3 |
| Sucrose | 0 |
| d-Trehalose | 0 |
| d-Xylose | 3 |
| Dextrose | 3 |
| Negative Control | 0 |

*3 = Good utilization
2 = Fair utilization
1 = Poor utilization
0 = No utilization It is to be understood that for the production of BL580Δ, the present invention is not limited to this particular microorganism or to microorganisms fully answering the growth and microscopic characteristics of NRRL 8180. In fact, it is desired and intended to include the use of mutants produced from NRRL 8180 by various means, such as X-radiation, ultraviolet radiation, nitrogen mustard, phage exposure and the like.

Antibiotic BL580Δ is highly effective in controlling coccidial infections in a warm blooded animal host. Furthermore, antibiotic BL580Δ is markedly less toxic than antibiotic BL580α (whose structure is set forth in Netherlands Patent No. 7,402,938). The activity of antibiotic BL580Δ as an anticoccidial agent was demonstrated by the following in vivo tests wherein the following poultry diet was used.

| | |
|---|---|
| Vitamin-Amino Acid Premix | 0.5% |
| Trace Minerals | 0.1% |
| Sodium Chloride | 0.3% |
| Dicalcium Phosphate | 1.2% |
| Ground Limestone | 0.5% |
| Stabilized Fat | 4.0% |
| Dehydrated Alfalfa (17% protein) | 2.0% |
| Corn Gluten Meal (41% protein) | 5.0% |
| Menhaden Fish Meal (60% protein) | 5.0% |
| Soybean Oil Meal (44% protein) | 30.0% |
| Ground Yellow Corn, fine to | 100% |

The vitamin-amino acid premix in the above poultry diet was prepared from the following formulation. The expressions of quantity relate to units per kilogram of the poultry diet.

| | | |
|---|---|---|
| Butylated Hydroxy Toluene | 125 | mg |
| dl-Methionine | 500 | mg |
| Vitamin A | 3300 | I.U. |
| Vitamin D$_3$ | 1100 | I.C.U. |
| Riboflavin | 4.4 | mg |
| Vitamin E | 2.2 | I.U. |
| Niacin | 27.5 | mg |
| Pantothenic Acid | 8.8 | mg |
| Choline Chloride | 500 | mg |
| Folic Acid | 1.43 | mg |
| Menadione Sodium Bisulfate | 1.1 | mg |
| Vitamin B$_{12}$ | 11 | mcg |
| Ground Yellow Corn, fine to | 5 | gm |

MIXED COCCIDIA INFECTIONS OF *EIMERIA TENELLA* AND *EIMERIA ACERVULINA*

A mixed inoculum of 5000 sporulated oocysts of *Eimeria acervulina* and a sufficient number of oocysts of *Eimeria tenella* to produce 85% to 100% mortality in untreated controls was given to groups of seven-day-old chicks, by direct inoculation into the crops of all chicks. The chicks were given free access to the poultry diet and water during the entire test period. Two days after inoculation, medicated feed, composed of the poultry diet and several levels of BL580Δ, was presented to the various groups of chicks in the test. Ten days after inoculation the tests were terminated. The chicks were weighed, necropsied and their intestinal tracts examined for lesions. The results of this test appear in Table V. These results show that 100% survival of infected chicks was obtained when 125 ppm or 250 ppm of BL580Δ was administered to infected chicks in their diet. These results also show a significant suppression of lesions due to *Eimeria tenella* and *Eimeria acer-*

*vulina* when 30 ppm or 60 ppm of BL580Δ is administered to infected chicks in their diet.

Table V

| Concentration of BL580Δ in Diet ppm | Number of Birds Started | Percent Survival | Percent Birds with Reduced Lesions | |
|---|---|---|---|---|
| | | | *Eimeria tenella* | *Eimeria acervulina* |
| 0 | 60 | 17 | 0 | 0 |
| 250 | 5 | 100 | 100 | 100 |
| 125 | 5 | 100 | 100 | 100 |
| 60 | 24 | 91.6 | 46 | 100 |
| 30 | 25 | 60 | 0 | 64 |

MIXED COCCIDIA INFECTION OF *EIMERIA TENELLA, EIMERIA ACERVULINA, EIMERIA NECATRIX, EIMERIA BRUNETTI* AND *EIMERIA MAXIMA*

A commercial vaccine (Coccivac®D, Sterwin Laboratories, Opalika, Alabama) containing a mixture of at least five species of Eimeria coccidia, was administered to chicks at 70 times the normal immunizing dose. The vaccine was given to groups of seven-day-old chicks, by direct inoculation into the crops of all chicks. The chicks were given free access to water and the above poultry diet during the entire test period. Two days after inoculation medicated feed, composed of the poultry diet and several levels of BL580Δ, was presented to the various groups of chicks in the test. Ten days after inoculation the tests were terminated and the birds were weighed, necropsied and their intestinal tracks examined for lesions. The results of this test appear in Table VI. These results show that 100% survival of infected chicks is obtained when 120 ppm of BL580Δ is administered to infected chicks in their diet. This level also shows a significant supression of lesions due to *Eimeria tenella, Eimeria acervulina, Eimeria necatrix, Eimeria brunetti* and *Eimeria maxima*.

Table VI

| Concentration of BL580Δ in Diet ppm | Number of Birds Started | Percent Survival | Percent Birds with Reduced Lesions Eimeria species | | | | |
|---|---|---|---|---|---|---|---|
| | | | tenella | acervulina | necatrix | brunetti | maxima |
| 0 | 15 | 0 | 0 | 0 | 60 | 0 | 20 |
| 120 | 15 | 100 | 100 | 100 | 100 | 100 | 100 |
| 60 | 15 | 100 | 40 | 93 | 100 | 48 | 80 |
| 30 | 15 | 100 | 7 | 7 | 86 | 0 | 21 |

FERMENTATION PROCESS

Cultivation of the microorganism *Streptomyces hygroscopicus* NRRL 8180 may be carried out in a wide variety of liquid culture media. Media which are useful for the production of antibiotic BL580Δ include an assimilable source of carbon such as starch, sugar, molasses, glycerol, etc.; an assimilable source of nitrogen such as protein, protein hydrolysate, polypeptides, amino acids, corn steep liquor, etc.; and inorganic anions and cations such as potassium, sodium, calcium, sulfate, phosphate, chloride, etc. Trace elements such as boron, molybdenum, copper, etc. are supplied as impurities of other constituents of the media. Aeration in tanks and bottles is provided by forcing sterile air through or onto the surface of the fermenting medium. Further agitation in tanks is provided by a mechanical impeller. An antifoaming agent such as one percent octadecanol in lard oil may be added as needed.

INOCULUM PREPARATION

Shaker flask inoculum of *Streptomyces hygroscopicus* NRRL 8180 is prepared by inoculating 100 ml portions of sterile liquid medium in 500 ml flasks with scrapings or washings of spores from an agar slant of the culture. The following medium is ordinarily used:

| | |
|---|---|
| Soy flour | 1.0% |
| Glucose | 2.0% |
| Corn steep liquor | 0.5% |
| CaCO$_3$ | 0.3% |
| Water    qs | 100% |

The flasks are incubated at a temperature from 25° C. to 29° C., preferably 28° C. and agitated vigorously on a rotary shaker for 48 to 96 hours.

Two 100 ml portions of this inoculum are used to noculate 12 liters of the same sterile medium in a 20 liter bottle. This inoculum is incubated with agitation and aeration of sterile air for 36 to 64 hours at 25° C. to 29° C., preferably 28° C.

This inoculum is used to inoculate 300 liters of the same sterile medium in a tank fermentor. This inoculum is incubated with agitation and aeration of sterile air for 36 to 64 hours at 25° C. to 29° C., preferably 28° C.

This inoculum is used to inoculate a 4000 liter fermentation tank containing 3000 liters of a sterile medium such as the following:

| | |
|---|---|
| Corn steep liquor | 0.5% |
| Soy flour | 1.0% |
| Corn starch | 4.0% |
| CaCO$_3$ | 0.1% |
| Water    qs | 100% |

This medium is fermented for 100 to 200 hours at a temperature of 27° C. to 32° C. with agitation by an impeller and aeration at a rate of 0.4–0.8 liters of air per liter of medium per minute. Normally a defoamer such as Hodag FD82 is added at a ratio of about 1.3 gal./1000 gal. of medium.

PURIFICATION PROCEDURE

After the fermentation is completed, the fermented mash containing antibiotic BL580Δ is combined with about one-half its volume of ethyl acetate and stirred for 2–3 hours. An approximate 8% portion of diatomaceous earth is added and the mixture is filtered through a plate and frame filter press. The cake is washed on the press with ethyl acetate. The ethyl acetate extracts are collected and concentrated in a still to a syrup.

The above syrup is stirred with twice its volume of heptane and stored at 4° C. overnight. The supernatant is recovered by decantation and concentrated to a gummy residue.

The gummy concentrate is treated with 10 liters of methanol and chilled with the aid of dry ice for several hours. The mixture is filtered through sintered glass with diatomaceous earth precoat and washed with cold methanol. The methanol solution is concentrated to dryness in vacuo.

A chromatographic column is prepared with activated carbon at a ratio of about one liter of carbon per 50 g of charge. The dried residue is dissolved in methylene chloride at a ratio of 40 g/liter and charged on the column. The methylene chloride eluate is collected as one cut and concentrated to dryness. The residue is mixed with methanol and stored in a chill room with dry ice to reduce the temperature to −10° C. for 15 minutes. After 15 minutes the solidified oil is filtered off and the methanol soluble material is concentrated to dryness in vacuo giving an oil.

This oil is dissolved in a minimum amount of methylene chloride, combined with silica gel, concentrated to dryness and charged on a dry silica gel column. The column is developed with 10% ethyl acetate in benzene followed by 20% ethyl acetate in benzene. The column is then allowed to drain. The column is measured into 10 equal parts (including the charge). Core samples are removed at Rf 0.05, 0.15, 0.25, 0.35 . . . etc., for the length of the entire column and eluted with an appropriate volume of ethyl acetate:methylene chloride:methanol (2:2:1). At places where the antibiotic overlaps, core sampling is done at every ⅛ of an Rf unit. The antibiotic is located by thin layer chromatography of the core eluates on commercially available thin layer plates (Silplate-22 distributed by Brinkmann Instrument Co., Westbury, N.Y. 11590). The respective zones were detected by charring in the presence of sulfuric acid.

The section of the column comprising Rf 0.11 to 0.34 is excised from the column and slurried in ethyl acetate:-methylene chloride:methanol (2:2:1 by volume). This mixture is filtered, washed with additional solvent mixture and concentrated in vacuo to dryness. The residue is dissolved in t-butanol, filtered and freeze dried to give a fluffy solid.

A two phase system is prepared by mixing n-heptane:methanol:ethyl acetate:water (3000:1500:75:37 by volume). Celatom (Eagle-Picher Industries, Cincinnati, Ohio), a brand of diatomaceous earth, is mixed with the lower phase of this system at a ratio of about 800 g/600 ml of lower phase and packed in increments into a (7.5 cm in diameter) column. The charge is applied as a mixture of diatomaceous earth, lower phase and lyophillized product (40 g:30 ml:13.8 g). The charged column is developed with upper phase and fractions of 25 ml are collected. The activity is detected by thin layer chromatography on selected fractions using a gelplate, chloroform:ethyl acetate (1:1) as developer and charring for detection. Fractions 90–150 are combined and concentrated giving antibiotic BL580Δ.

The invention will be described in greater detail in conjunction with the following specific examples.

EXAMPLE 1

Inoculum Preparation

A typical medium used to grow the primary inoculum is prepared according to the following formula:

| | |
|---|---|
| Soy flour | 1.0 g |
| Glucose | 2.0 g |
| Corn steep liquor | 0.5 g |
| CaCO$_3$ | 0.3 g |
| Water to | 100 ml |

The washed or scraped spores from an agar slant of *Streptomyces hygroscopicus* NRRL 8180 are used to inoculate two 500 ml flasks each containing 100 ml of the above medium which has been sterilized. The flasks are placed on a rotary shaker and agitated vigorously for 72 hours at 28° C.

The resulting flask inoculum is transferred to a 5 gallon glass bottle containing 12 liters of the same sterile medium. This secondary inoculum is aerated with sterile air while growth is carried out for 48 hours at 28° C.

The resulting secondary inoculum is transferred to a 100 gallon tank containing 300 liters of the same sterile medium. This tertiary inoculum is aerated with sterile air at the rate of one liter of air/liter of medium/minute and agitated by an impeller operating at 173 rpm. Growth is continued for 48 hours at 28° C. The pH at this time is 6.9 to 7.0.

EXAMPLE 2

Fermentation

A fermentation medium is prepared according to the following formula:

| | |
|---|---|
| Corn steep liquor | 0.5 g |
| Soy flour | 1.0 g |
| Corn starch | 4.0 g |
| CaCO$_3$ | 0.1 g |
| Water to | 100 ml |

A 3000 liter batch of fermentation medium of the above formulation in a 4000 liter tank is sterilized at 120° C. for 60 minutes. The ph of the medium after sterilization is 6.4 to 6.5. This medium is inoculated with 300 liters of tertiary inoculum prepared as described in Example 1. The fermentation is carried out at 28°–30° C., using 4.0 liters of Hodag FD82 as a defoaming agent. Aeration is supplied at the rate of 0.6 liter of sterile air per liter of mash per minute. The mash is agitated by an impeller driven at 150 rpm. At the end of 138.5 hours of fermentation time the mash is harvested.

EXAMPLE 3

Isolation and Purification

A 2550 liter portion of fermented mash prepared as described in Example 2, having a pH of 7.4 is combined with 1275 liters of ethyl acetate and stirred for 2.5 hours. An 8% (by weight) portion of diatomaceous earth is added. The mixture is filtered in several portions, with stirring, through a pair of frame presses. The aqueous-ethyl acetate filtrates are pooled providing 3250 liters which is allowed to separate, providing 1000 liters of ethyl acetate extract. After each portion of mash-ethyl acetate-diatomaceous earth is filtered through a press, the pad is washed on the press with ethyl acetate. The ethyl acetate washings are combined and separated giving 535 liters of ethyl acetate washings. The 1000 liters of ethyl acetate extracts and 535 liters of ethyl acetate washings are combined and concentrated in a 400 gallon still to 225 liters. This 225 liters if further concentrated in a 50 gallon still to 20 liters. This 20 liters is further concentrated in a glass still to a syrup.

The syrup is stored at 4° C. for 48 hours and then stirred with twice its volume of heptane. The mixture is allowed to stand at 4° C. overnight. The supernatant is recovered by decantation and concentrated to a gummy residue.

A 10 liter portion of methanol is added to the gummy residue and the mixture is chilled with the aid of dry ice for several hours. The mixture is filtered through sintered glass containing a diatomaceous earth precoat and washed with cold methanol. The combined filtrate and washings are concentrated to dryness in vacuo providing 1353.5 g of residue.

The 1353.5 g of residue is dissolved in methylene chloride at a rate of 40 g/liter. A chromatographic column is prepared by packing with 27.07 liters of 20×40 mesh granular carbon. The residue in methylene chloride is passed through this column at a flow rate of 375–400 ml per minute. The methylene chloride eluate is collected as one cut and concentrated to dryness giving 1053 g of residue. The residue is thoroughly mixed with 8–9 liters of methanol. The mixture is reduced to $-10°$ C. in a chill room with the aid of dry ice and maintained at $-10°$ C. for 15 minutes. Any solidified oil is removed by filtration and the methanol filtrate is concentrated to dryness in vacuo giving 781.4 g as an oil.

A dry pack chromatographic column is prepared by packing 4 kg of silica gel onto a 12" circumference plastic column. A 200 g portion of the above oil is dissolved in a minimal amount of methylene chloride. A 300 g portion of silica gel is added and mixed thoroughly and the mixture is then concentrated in vacuo to dryness. The dried mixture is charged on the column and some sea sand is placed on the top of the column to prevent bed disturbance during elution. The plastic column is placed in a glass shell to give it support. The column is eluted with 12 liters of 10% ethyl acetate in benzene. The column is allowed to run dry and then eluted with 7.6 liters of 20% ethyl acetate in benzene. Cuts are collected and the column is allowed to run dry. The column is then purged with nitrogen. Antibiotic activity is determined by assaying the cuts vs *Streptococcus pyogenes* NY5. The column is measured into 10 equal parts (including the charge). Core samples are removed at Rf 0.05, 0.15, 0.25, 0.35 . . . etc., for the length of the entire column. At places where the antibiotic bands overlapped, core sampling is done at every $\frac{1}{8}$ of an Rf unit. Each core sample is eluted with 10 ml of ethyl acetate:methylene chloride:methanol (2:2:1) and examined by thin layer chromatography using the system ethyl acetate:chloroform (1:1) spotting 30λ of sample and charring with sulfuric acid. The section of column Rf 0.11 to Rf 0.34 is removed and slurried in ethyl acetate:methylene chloride:methanol (2:2:1). The mixture is filtered and washed with the same solvent mixture and concentrated to dryness in vacuo. The residue is dissolved in t-butanol, filtered and lyophilized giving 26.7 g.

A two-phase system is prepared by mixing n-heptane:methanol:ethyl acetate:water [3000:1500:75:37 (by volume)]. An 800 g portion of acid washed diatomaceous earth is mixed with 600 ml of the lower phase of this solvent system and packed in increments into a 7.5 cubic inch glass column. The charge, comprising 40 g of diatomaceous earth, 30 ml of lower phase solvent and 13.8 g of the above lyophilized material, is applied as a mixture. The charged column is developed with the upper phase of the solvent system and 25 ml fractions are collected. The desired compound is located by assaying fraction samples as above with thin layer chromatography. Fractions 90–150 are combined and lyophilized providing 2.75 g of the product BL580Δ primarily as the sodium salt.

EXAMPLE 4

Preparation and Isolation of BL580Δ as the Free Acid

The partial sodium salt of BL580Δ is prepared and isolated as described in Examples 1–3. A two phase system is prepared by mixing heptane, methanol, ethyl acetate, water (3000:1500:80:40 by volume). A glass column is packed with a mixture of 800 g of diatomaceous earth and 600 ml of the lower phase of the above system. The charge is applied as a mixture of 28 g of diatomaceous earth, 21 ml of lower phase and 10.9 g of the BL580Δ partial sodium salt. The column is developed with upper phase. Fractions of 90 ml volume are collected. Selected fractions are chromatographed on Silphate® F-22 using ethyl acetate:chloroform as developer and charring for detection in order to locate the BL580Δ. Fractions 29–39, containing the BL580Δ are combined and the solvent is removed. The resulting solid is redissolved in t-butanol and lyophilized giving 4.79 g.

An 800 mg portion of this lyophilized material is stirred in 300 ml of a two phase system composed of water:ether:petroleum ether (2:1:1). The pH is adjusted to 2.5 using 1N HCl while stirring. The organic phase is separated and washed three times with an equal volume of water. The solvent extract is concentrated in vacuo to a residue. The residue is dissolved in t-butanol and then lyophilized giving 657 mg of BL580Δ as the free acid.

The free acid of BL580Δ has microanalytical data as follows: C, 61.10; H, 8.9; ash, 0; and a specific rotation $[\alpha]_D^{25} = +21° \pm 1°$ (C=0.9 in methanol).

The free acid of BL580Δ exhibited characteristic absorption in the infrared region of the spectrum at the following wavelengths: 2.95; 5.88; 8.35; 8.60; 9.00; 9.12; 9.43; 9.62; 10.05; and 10.47μ.

A standard infrared absorption spectrum of the free acid of BL580Δ prepared in a KBr pellet is shown in FIG. 4 of the accompanying drawings.

A standard proton magnetic resonance spectrum of the free acid of BL580Δ is shown in FIG. 5 of the accompanying drawings.

A standard $^{13}C$ nuclear magnetic resonance spectrum of the free acid of BL580Δ is shown in FIG. 6 of the accompanying drawings.

·EXAMPLE 5

Preparation of the Sodium Salt of BL580Δ

BL580Δ free acid (1 g) is dissolved in 300 ml of ether-petroleum ether (1:1). This solution is added to 200 ml of water to give a two-phase system. The pH is adjusted to 10.0 by the addition of 0.1 N NaOH while stirring, after which the organic phase is separated and concentrated in vacuo to a residue. The residue is dissolved in 10 ml of ether and 20 ml of petroleum ether (30°–70° C.) is added. The resulting solution is seeded with a crystal of BL580Δ sodium salt and allowed to evaporate slowly at 4° C. until a crystalline solid forms. The crystals are collected on a filter, washed with cold petroleum ether and air dried to yield 323 mg of the sodium salt of BL580Δ.

This sodium salt of antibiotic BL580Δ has a melting point of 157°–161° C.; C, 60.99; H, 8.47; Na, 1.95; $[\alpha]_D^{25} = +6° \pm 1°$ (C=1.153 in methanol). The sodium salt of BL580Δ exhibited characteristic absorption in the infrared region of the spectrum at the following wavelengths: 6.27, 7.28, 9.0, 9.13, 9.23, 9.48 and 10.60μ.

A standard infrared absorption spectrum of the sodium salt of BL580Δ prepared in a KBr pellet is shown in FIG. 1 of the accompanying drawings.

A standard $^{13}C$ nuclear magnetic resonance spectrum of the sodium salt of BL580Δ is shown in FIG. 2 of the accompanying drawings.

A standard proton magnetic resonance spectrum of the sodium salt of BL580Δ is shown in FIG. 3 of the accompanying drawings.

EXAMPLE 6

Preparation and Isolation of the p-Bromophenacyl Ester of BL580Δ

The partial sodium salt of BL580Δ is prepared and isolated as described in Examples 1–3. A one gram portion of this BL580Δ sodium salt, 834 mg of p-bromophenacyl bromide, 600 mg of lithium carbonate and 20 ml of dry dimethylformamide are placed in a flask and allowed to react at 37° C. for 16 hours. Four volumes of chloroform are added and the resulting suspension is filtered. The filtrate is concentrated in vacuo to remove the solvent giving a syrupy residue. A diatomaceous earth partition column is prepared using a system composed of heptane:ethyl acetate:methanol:water (2000:25:1000:17). A 120 g portion of diatomaceous earth and 90 ml of lower phase are used for the column. The syrupy residue, 12 g of diatomaceous earth and 9 ml of lower phase are applied to the top of the column. The column is developed with upper phase. Fractions of 10 ml each are collected. The activity in the fractions is located by thin layer chromatography. Fractions 22–41 are combined and concentrated in vacuo to a residue. The residue is dissolved in 50 ml of methanol and filtered. The filtrate is warmed on a steam bath, 10 ml of water is added and the mixture is allowed to cool slowly to 4° C. The resulting crystals are collected giving 566 mg of BL580Δ as the p-bromophenacyl ester.

The p-bromophenacyl ester of BL580Δ has microanalytical data as follows: C, 58.80; H, 7.80; Br, 8.64; a specific rotation $[\alpha]_D^{25} = +63° \pm 2°$ (CHCl$_3$ at 0.51%).

The p-bromophenacyl ester of BL580Δ exhibited characteristic absorption in the infrared region of the spectrum at the following wavelengths: 2.95; 5.88; 6.30; 8.20; 8.45; 8.60; 9.00; 9.15 (broad); 9.37 (broad); 9.62; 10.06; and 10.37.

The molecular weight of the p-bromophenacyl ester of BL580Δ monohydrate is 1114±0.3% as determined by X-ray diffraction.

A standard infrared absorption spectrum of the p-bromophenacyl ester of BL580Δ prepared in a KBr pellet is shown in FIG. 7 of the accompanying drawings.

A standard ultraviolet absorption spectrum of the p-bromophenacyl ester of BL580Δ prepared at a concentration of 35.84 mcg/ml in methanol is shown in FIG. 8 of the accompanying drawings.

A standard proton magnetic resonance spectrum of the p-bromophenacyl ester of BL580Δ is shown in FIG. 9 of the accompanying drawings.

We claim:

1. A process for the production of antibiotic BL580 Δ of the formula:

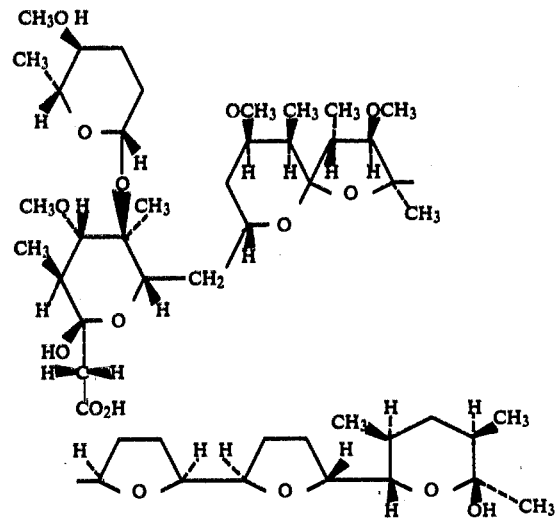

which comprises cultivating Streptomyces hygroscopicus NRRL 8180 or mutants thereof in an aqueous nutrient medium containing assimilable sources of carbohydrate, nitrogen, and inorganic salts under submerged aerobic conditions until substantial antibiotic activity is imparted to said medium, and then recovering antibiotic BL580Δ therefrom.

* * * * *